United States Patent [19]

Nelson

[11] 4,012,431
[45] Mar. 15, 1977

[54] PROCESS FOR PREPARING 5-OXA PGF$_1\alpha$ -TYPE COMPOUNDS

[75] Inventor: Norman A. Nelson, Galesburg, Mich.

[73] Assignee: The Upjohn Company, Kalamazoo, Mich.

[22] Filed: Dec. 6, 1974

[21] Appl. No.: 530,086

Related U.S. Application Data

[62] Division of Ser. No. 361,991, May 21, 1973, Pat. No. 3,931,279.

[52] U.S. Cl. .................. 260/468 D; 260/514 D
[51] Int. Cl.$^2$ .............. C07C 51/00; C07C 177/00
[58] Field of Search ............ 260/468 D, 514 D, 69

[56] References Cited

UNITED STATES PATENTS 3,887,587   6/1975   Schaaf et al. .................. 260/345.8
3,923,862   12/1975   Nelson ........................... 260/468

OTHER PUBLICATIONS

Fiesen et al. Reagent For Organic Synthesis, p. 261 (1967).
DeWolfe, Carboxylic Ortho Acid Derivatives pp. 18, 19 (1970).

*Primary Examiner*—Robert Gerstl
*Attorney, Agent, or Firm*—Morris L. Nielson

[57] ABSTRACT

Process for making 5-oxa prostaglandin F$_1$ $\alpha$ -type compounds. These compounds are useful for a variety of pharmacological purposes, including inhibition of platelet aggregation, increase of nasal patency, and labor inducement at term.

10 Claims, No Drawings

PROCESS FOR PREPARING 5-OXA PGF$_{1\alpha}$-TYPE COMPOUNDS

CROSS REFERENCE TO RELATED APPLICATIONS

This application is a divisional of my co-pending application Ser. No. 361,991 filed May 21, 1973 now U.S. Pat. No. 3,931,279.

BACKGROUND OF THE INVENTION

This invention relates to novel compositions of matter, to novel methods for producing those, and to novel chemical intermediates useful in those processes. Particularly, this invention relates to a process for preparing certain novel analogs of prostaglandin $F_{1\alpha}$ in which the C-5 methylene (—CH$_2$) in the prostanoic acid structure is replaced by oxygen (—O—), represented by the formula:

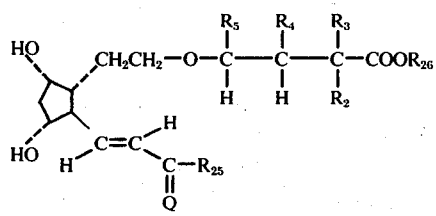

wherein the terms O, $R_2$, $R_3$, $R_4$, $R_4$, $R_{25}$, and $R_{26}$ are defined herein.

The essential material for this application, including the background of the invention, the disclosure of the invention, and the description of the preferred embodiments, including Preparations and Examples, is incorporated by reference from U.S. Pat. No. 3,931,279 columns 1–67 and 73–86, inclusive, under the provisions of M.P.E.P. 608.01(p).

SUMMARY OF THE INVENTION

It is a purpose of this invention to provide novel 5-oxa prostagalandin E, F, A, and B analogs. It is a further purpose to provide novel 5-oxa prostaglandin analogs with a variety of substituents and degrees of saturation in the side chains. It is a further purpose to provide 5-oxa prostaglandin analogs having the 11-deoxy ring-structure in which the 11-hydroxy is replaced by hydrogen. It is a further purpose to provide esters, lower alkanolates, and pharmacologically acceptable salts of said analogs. It is a further purpose to provide novel processes for preparing said analogs and esters. It is still a further purpose to provide novel intermediates useful in said processes.

The novel prostaglandin analogs of this invention each have an oxygen (—O—) in place of the methylene (—CH$_2$—) moiety at the 5-position of the prostanoic acid formula. They are represented by the generic formula

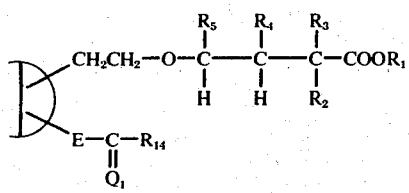

VII wherein D is one of the six carbocyclic moieties:

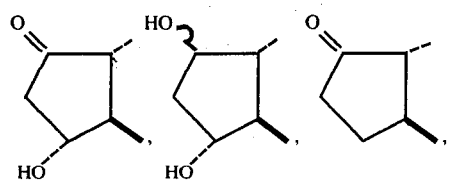

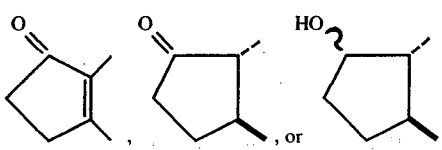

wherein ~ indicates alpha or beta attachment of hydroxyl to the cyclopentane ring; wherein E is —CH$_2$CH$_2$— or

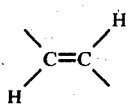

wherein $Q_1$ is

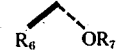

or

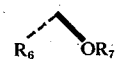

wherein $R_6$ and $R_7$ are hydrogen or alkyl of one to 4 carbon atoms, inclusive, being the same or different; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein $R_3$ is hydrogen, alkyl of one to 4 carbon atoms, inclusive, or fluoro; wherein $R_2$ is hydrogen or fluoro, with the proviso that $R_2$ is fluoro only when $R_3$ is hydrogen or fluoro; wherein $R_4$ and $R_5$ are hydrogen or alkyl of one to 4 carbon atoms, inclusive, being the same or different with the proviso that no more than one of $R_3$, $R_4$, and $R_5$ is alkyl; and wherein $R_{14}$ is (1)

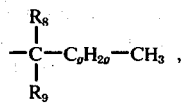

(2) 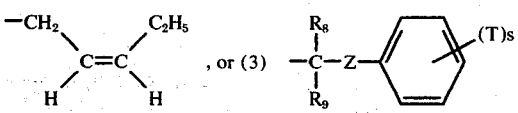

with the proviso that $R_{14}$ is

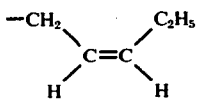

only when E is

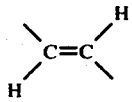

; wherein $C_gH_{2g}$ is alkylene of one to 9 carbon atoms, inclusive, with one to 5 carbon atoms, inclusive, in the chain between —$CR_8R_9$— and terminal methyl; wherein $R_8$ and $R_9$ are hydrogen, alkyl of one to 4 carbon atoms, inclusive, or fluoro, being the same or different, with the proviso that $R_9$ is fluoro only when $R_8$ is hydrogen or fluoro; wherein T is alkyl of one to 4 carbon atoms, inclusive, fluoro, chloro, trifluoromethyl, or —$OR_{10}$, wherein $R_{10}$ is hydrogen or alkyl of one to 4 carbon atoms, inclusive, and s is zero, one, 2, or 3, with the proviso that not more than two T's are other than alkyl; and wherein Z represents an oxa atom (—O—) or $C_jH_{2j}$, wherein $C_jH_{2j}$ is a valence bond or alkylene of one to 9 carbon atoms, inclusive, substituted with zero, one, or 2 fluoro, with one to 6 carbon atoms, inclusive, between —$CR_8R_9$— and the ring.

I claim:
1. A process for preparing an optically active compound of the formula

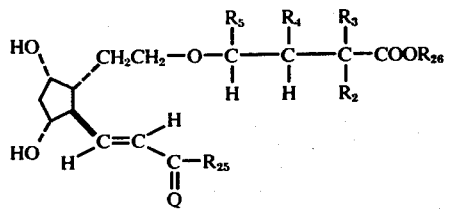

or a racemic compound of that formula and the mirror image thereof, wherein $Q_2$ is

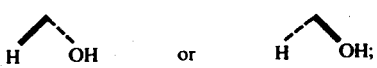

wherein $R_3$ is hydrogen, alkyl of one to 4 carbon atoms, inclusive, or fluoro; wherein $R_2$ is hydrogen or fluoro, with the proviso that $R_2$ is fluoro only when $R_3$ is hydrogen or fluoro; wherein $R_4$ and $R_5$ are hydrogen or alkyl of one to 4 carbon atoms, inclusive, being the same or different, with the proviso that not more than one of $R_3$, $R_4$, and $R_5$ are alkyl; wherein $R_{25}$ is

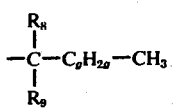

(1)

wherein $C_gH_{2g}$ is alkylene of one to 9 carbon atoms, inclusive, with one to 5 carbon atoms, inclusive, in the chain between —$CR_8R_9$— and terminal methyl, wherein $R_8$ and $R_9$ are hydrogen, alkyl of one to 4 carbon atoms, inclusive, or fluoro, being the same or different, with the proviso that $R_9$ is fluoro only when $R_8$ is hydrogen or fluoro, or (2)

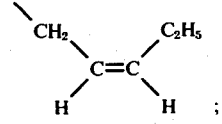

;

and wherein $R_{26}$ is alkyl of one to 3 carbon atoms, inclusive; which comprises starting with an optically active compound of the formula
a. condensation with an omega-halo ortho ester of the formula

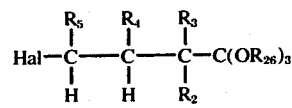

wherein Hal is chloro, bromo, or iodo, and wherein $R_2$, $R_3$, $R_4$, $R_5$, and $R_{26}$ are as defined above, in the presence of a base selected from the class consisting of n-butyllithium, phenyllithium, triphenylmethyllithium, sodium hydride, and potassium t-butoxide, and, when the base is an organolithium compound, in dimethyl formamide or hexamethylphosphoramide;
b. transformation of the product of step a) to an optically active compound of the formula

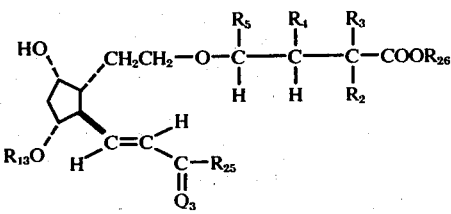

or a racemic compound of that formula and the mirror image thereof, wherein $Q_3$, $R_2$, $R_3$, $R_4$, $R_5$, $R_{13}$, $R_{25}$, and $R_{26}$ are as defined above, by hydrolysis; and
c. replacement of the $R_{13}$ groups with hydrogen, by hydrolysis.

2. The process of claim 1 wherein the condensation of step a) is done in the presence of potassium t-butoxide.

3. The process of claim 1 wherein the condensation of step a) is done in the presence of n-butyllithium and hexamethylphosphoramide.

4. A process according to claim 1 wherein $R_3$, $R_4$, and $R_5$ are either hydrogen or methyl, and at least one of $R_3$, $R_4$, and $R_5$ is methyl.

5. A process according to claim 1 wherein $R_2$, $R_3$, $R_4$, and $R_5$ are hydrogen.

6. A process according to claim 5 wherein $R_8$ and $R_9$ are either hydrogen or methyl, and at least one of $R_8$ and $R_9$ is methyl.

7. A process according to claim 5 wherein $C_gH_{2g}$ is trimethylene.

8. A process according to claim 5 wherein $R_{25}$ is

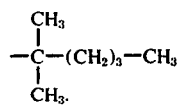
9. A process according to claim 5 wherein $R_{25}$ is $-(CH_2)_4-CH_3$.
10. A process according to claim 5 wherein $R_{25}$ is
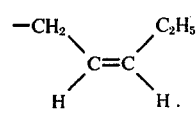
* * * * *

UNITED STATES PATENT OFFICE
CERTIFICATE OF CORRECTION

Patent No. 4,012,431     Dated   March 15, 1977

Inventor(s)   Norman A. Nelson

It is certified that error appears in the above-identified patent and that said Letters Patent are hereby corrected as shown below:

Column 1, line 30:   "O" should read -- Q --.

Column 1, line 49:   "alkanolates" should read -- alkanoates --.

Column 2, lines 6-8:  

Column 4, line 15:   "blank" should read --

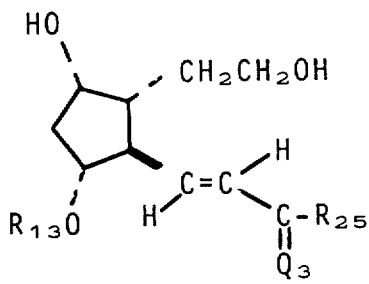

or a racemic compound of that formula and the mirror image thereof, wherein $Q_3$ is

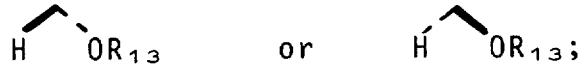

wherein $R_{13}$ is selected from the group consisting of (a) tetrahydropyranyl, (b) tetrahydrofuranyl; or (c) a group of the formula

UNITED STATES PATENT AND TRADEMARK OFFICE
CERTIFICATE OF CORRECTION

PATENT NO. : 4,012,431
DATED : March 15, 1977
INVENTOR(S) : Norman A. Nelson

It is certified that error appears in the above—identified patent and that said Letters Patent are hereby corrected as shown below:

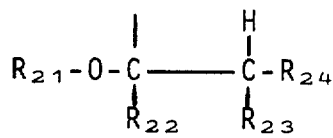

wherein $R_{21}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{22}$ and $R_{23}$ are the same or different, being hydrogen, alkyl of one to 4 carbon atoms, inclusive, or, when $R_{22}$ and $R_{23}$ are taken together, $-(CH_2)a-$ or $-(CH_2)b-O-(CH_2)c-$ wherein a is 3, 4, or 5, b is one, 2, or 3, and c is one, 2, or 3 with the proviso that b plus c is 2, 3, or 4, and wherein $R_{24}$ is hydrogen or phenyl; and wherein $R_{25}$ is as defined above; and subjecting said compound successively to the following reactions:

Signed and Sealed this

Twenty-ninth Day of November 1977

[SEAL]

Attest:

RUTH C. MASON
*Attesting Officer*

LUTRELLE F. PARKER
*Acting Commissioner of Patents and Trademarks*